(12) United States Patent
Zhu et al.

(10) Patent No.: US 11,460,402 B2
(45) Date of Patent: Oct. 4, 2022

(54) METHODS FOR DETECTING AND QUANTIFYING GLUTARALDEHYDE-BASED PRODUCTS IN WATER

(71) Applicant: Saudi Arabian Oil Company, Dhahran (SA)

(72) Inventors: Xiangyang Zhu, Dhahran (SA); Mohammed A. Al-Moniee, Dhahran (SA); Mazen A. Al-Saleh, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 127 days.

(21) Appl. No.: 17/080,453

(22) Filed: Oct. 26, 2020

(65) Prior Publication Data

US 2022/0128468 A1 Apr. 28, 2022

(51) Int. Cl.
*G01N 21/64* (2006.01)
*G01N 33/18* (2006.01)
(Continued)

(52) U.S. Cl.
CPC ......... *G01N 21/6428* (2013.01); *A01N 35/02* (2013.01); *G01N 33/1826* (2013.01);
(Continued)

(58) Field of Classification Search
CPC .......... G01N 21/6428; G01N 33/1826; G01N 2021/6432; G01N 2021/7786;
(Continued)

(56) References Cited

U.S. PATENT DOCUMENTS

| 6,840,052 B2 | 1/2005 | Smith et al. |
| 3,038,937 A1 | 10/2011 | Kelly et al. |

(Continued)

FOREIGN PATENT DOCUMENTS

| CN | 105115961 B | 2/2018 |
| DE | 19719927 A1 | 11/1998 |

(Continued)

OTHER PUBLICATIONS

Nguyen et al., "Biofouling of Water Treatment Membranes: A Review of the Underlying Causes, Monitoring Techniques and Control Measures", Membranes 2012, 2, 804-840 (Year: 2012).*

(Continued)

*Primary Examiner* — Samuel P Siefke
*Assistant Examiner* — Henry H Nguyen
(74) *Attorney, Agent, or Firm* — Leason Ellis LLP (57) ABSTRACT

A method for detecting glutaraldehyde in a water sample in which Au-BSA nanoclusters have been introduced is provided. In the method, the water sample is mixed with the Au-BSA nanoclusters to form a mixture. The mixture is incubated for 2 to 10 minutes, and the glutaraldehyde present in the mixture reacts with the Au-BSA nanoclusters and causes fluorescence quenching of the Au-BSA nanoclusters. Then a fluorescence intensity of the quenched Au-BSA nanoclusters in the mixture is measured at an emission wavelength of 675 nm. A presence and concentration of glutaraldehyde in the water sample is then determined by comparing the measured fluorescence intensity of the quenched Au-BSA nanoclusters at the emission wavelength of 675 nm with fluorescence intensity values of calibration samples comprising Au-BSA nanoclusters and known glutaraldehyde concentrations.

17 Claims, 7 Drawing Sheets

(51) Int. Cl.
*B82Y 15/00* (2011.01)
*G01N 21/77* (2006.01)
*A01N 35/02* (2006.01)
*B01D 15/34* (2006.01)

(52) U.S. Cl.
CPC ............... *B01D 15/34* (2013.01); *B82Y 15/00* (2013.01); *G01N 2021/6432* (2013.01); *G01N 2021/7786* (2013.01); *G01N 2033/184* (2013.01)

(58) Field of Classification Search
CPC .. G01N 2033/184; A01N 35/02; B01D 15/34; B82Y 15/00
See application file for complete search history.

(56) References Cited

U.S. PATENT DOCUMENTS

| | | | |
|---|---|---|---|
| 9,772,287 B2 | 9/2017 | Al-Moniee et al. | |
| 2006/0033910 A1* | 2/2006 | Sun | G01N 21/6428 356/301 |
| 2011/0165689 A1* | 7/2011 | Ying | G01N 21/643 252/301.36 |
| 2015/0300955 A1* | 10/2015 | Al-Moniee | G01N 21/643 436/128 |

FOREIGN PATENT DOCUMENTS

| | | |
|---|---|---|
| EP | 1282417 B1 | 1/2005 |
| EP | 3132261 A1 | 2/2017 |
| ES | 2340118 B1 | 4/2011 |
| KR | 20060052134 A | 5/2006 |
| WO | 2014087413 A1 | 6/2014 |
| WO | 2019043711 A1 | 3/2019 |

OTHER PUBLICATIONS

Anuwat Petdum, et al., "New Fluorescence Sensor for Online Monitoring of Copper (II) Ion in Food Supplements," 17th International Meeting on Chemical Sensors 2018. doi 10.5162/IMCS2018/P1AP.5.

Gros, Nataša. "A novel type of tri-colour light-emitting-diode-based spectrometric detector for low-budget flow-injection analysis." Sensors 7.2 (2007): 166-184.

No Author, "Instruction Manual, 91343-Quantofix-Glutaraldehyde", Quantofix: 1 page.

No Author, "Instruction Manual Glutaraldehyde Test Kit, Model GT-1", Hach: 1 page.

Liu, Mingxian, et al. "Recent progress on gold-nanocluster-based fluorescent probe for environmental analysis and biological sensing." Journal of analytical methods in chemistry 2019 (2019).

Liu, Yanlan, et al. "Gold-nanocluster-based fluorescent sensors for highly sensitive and selective detection of cyanide in water." Advanced Functional Materials 20.6 (2010): 951-956.

No Author, "NIOSH method 2532 HPLC for Glutaraldehyde", CDC, Aug. 15, 1994: 4 pages.

No Author. Poster List Day 1 "2019-CHEMINDIX—Oct. 29-31, 2019" 85 pages.

Wang, Xianxiang, et al. "Ultrasensitive fluorescence detection of glutaraldehyde in water samples with bovine serum albumin-Au nanoclusters" Microchemical Journal 99.2 (2011): 327-331.

Xie, Jianping, Yuangang Zheng, and Jackie Y. Ying. "Highly selective and ultrasensitive detection of Hg2+ based on fluorescence quenching of Au nanoclusters by Hg2+—Au+ interactions." Chemical Communications 46.6 (2010): 961-963.

Xie, Jianping, Yuangang Zheng, and Jackie Y. Ying. "Protein-directed synthesis of highly fluorescent gold nanoclusters." Journal of the American Chemical Society 131.3 (2009): 888-889.

International Search Report and Written Opinion in corresponding PCT Application No. PCT/US2021/056143, dated Jan. 25, 2022, 11 pages.

Nandi, Indrani et al.: Protein Fibril-Templated Biomimetic Synthesis of Highly Fluorescent Gold Nanoclusters and Their Applicatins in Cysteine Sensing, ACS OMEGA, vol. 3, No. 7, Jul. 31, 2018, pp. 7703-7714,http://pubs.acs.org/doi/pdf/10.1021/acsomega.8b01033.

Hemmateenejad, Bahram et al. BSA—modified gold nanoclusters for sensing of folic acid; Sensors and Actuators B: Chemical, vol. 199, Mar. 27, 2014 pp. 42-46, XP028850621, ISSN: 0925-4005, DOI: 10.1016/J.SNB.2014.03.075 abstract.

Yen, Yao-Te et al. A Photoluminescent Colorimetric Probe of Bovine Serum Albumin-Stabilized Gold Nanoclusters for New Psychoactive Substances: Cathinone Drugs in Seized Street Samples, Sensors, vol. 19, No. 16, Aug. 15, 2019, p. 3554, abstract, p. 4, line 1-line 2.

Fernandez-Iglesias Nerea et al: Synthesis, purification and mass spectrometric characterisation of a fluorescent Au 9 @BSA nanocluster and its enzymatic digestion by trypsin, Nanoscale, vol. 6, No. 2, Jan. 1, 2014, pp. 716-721, United Kingdom, ISSN: 2040-3364, DOI: 101039/C3NR04217K; https://pubs.rsc.org/en/content/articlepdf/2014/nr/c3nr04217k> p. 717, left-hand column, last paragraph—right-hand column, paragraph 1 abstract.

Ryo Tanaka et al., A novel enhancement assay for immunochromatographic test strips using gold nanoparticles; Analytical and Bioanalytical Chemistry, Springer, Berlin, De,vol. 385, No. 8, Jul. 13, 2006, pp. 1618-2650.

Xianxiang Wang et al., Ultrasensitive fluorescence detection of glutaraldehyde in water samples with bovine serum albumin-Au nanoclusters, Microchemical Journal, New York, NY, vol. 99, No. 2, Jun. 3, 2011, pp. 327-331.

Wu, Jiapeng et al., On-off-on gold nanocluster-based near infrared fluorescent probe for recognition of Cu (II) and vitamin C; Microchimica Acta, Springer Vienna, vol. 184, No. 5, Feb. 15, 2017, pp. 3115-1324.

* cited by examiner

METHODS FOR DETECTING AND QUANTIFYING GLUTARALDEHYDE-BASED PRODUCTS IN WATER

TECHNICAL FIELD

The present disclosure is generally related to method of detection and quantification of a biocide-based compound in water.

BACKGROUND OF THE DISCLOSURE

Glutaraldehyde (GLUT) is an active component in many biocide products commonly used in oil and gas industry for microbial control in water systems, including saltwater injection systems. GLUT-based biocides are generally considered environment-friendly since they are readily degradable. Biocidal performance generally depends on the concentration of the biocide and its contact time with microorganisms. Therefore, it is essential to monitor biocide residual concentration closely throughout its distribution network to ensure adequate microbial control.

The concentration of GLUT in GLUT-based biocides has traditionally been detected and quantified using commercial test kits or laboratory-based High-Performance Liquid Chromatograph (HPLC) methods with a UV detector. However, these methods are inadequate for online field detection of GLUT. For example, using a HACH® colorimetric/spectrophotometric commercial test kit involves boiling temperatures and a long reaction time, and only detects up to 200 ppm of GLUT. QUANTOFIX® commercial test strips are semi-quantitative, and its detection range (5000-25000 ppm) is outside of the normal biocide treatment concentration range and residual concentration range in actual water treatment facilities and water distribution networks (10 ppm to 1000 ppm of GLUT concentration). While HPLC methods are commonly used for environmental compliance methods, they are impractical for online field detection of GLUT. Specifically, detecting a UV-chromophore—as is needed for HPLC methods—is a challenge for an online field instrument because the requirements for power consumption and the lifetime of the light source are hard to meet. Furthermore, high sensitivity and linearity at low concentration range with a HPLC method imposes a problem for online measurement.

A further challenge for online field measurement of GLUT in a large water pipeline network is collecting water samples for biocide residual measurement at downstream locations of the pipeline network after a batch treatment of the biocide product is administered at an upstream location. This is due to difficulties in estimating the travel time of the biocide in the large pipeline network because of the complexity of pipeline network (e.g., number of branches, diameters of branches) and daily operation changes and fluctuations (e.g., flow rate). As a result, biocide residual concentration cannot be easily monitored in downstream locations of a complex pipeline network, especially in remote injection wells, making it difficult to effectively controlling microbes with biocide in pipeline networks.

As such, there is a need for an effective online field measurement method for biocides in oil and gas facilities. The present application addresses these and other challenges related detecting and measuring GLUT-based biocides in water networks of oil and gas facilities.

SUMMARY OF THE DISCLOSURE

In a first aspect, a method for detecting glutaraldehyde in a water sample in which Au-BSA nanoclusters have been introduced is provided. In the method, the water sample is mixed with the gold-bovine serum albumin (Au-BSA) nanoclusters to form a mixture. The mixture is incubated for 2 to 10 minutes, such that glutaraldehyde present in the water sample quenches the Au-BSA nanoclusters. A fluorescence intensity of the quenched Au-BSA nanoclusters in the mixture is measured at an emission wavelength of 675 nm. A presence of glutaraldehyde in the water sample is then determined by comparing the measured fluorescence intensity of the quenched Au-BSA nanoclusters at the emission wavelength of 675 nm with fluorescence intensity values of calibration samples comprising Au-BSA nanoclusters and known glutaraldehyde concentrations.

In another aspect, the step of determining the presence of glutaraldehyde in the water sample includes calculating a concentration of glutaraldehyde in the water sample based on the correlation between the known GLUT concentrations and the fluorescence intensity of the quenched Au-BSA nanoclusters measured at the emission wavelength of 675 nm. In a further aspect, the calculated concentration of glutaraldehyde is accurate for water samples having a glutaraldehyde content of 10-1000 ppm.

In another aspect, the water is fresh water or salt water. In a further aspect, the salt water is Arabian Gulf Seawater.

In another aspect, the mixture is incubated in a temperature range of approximately 20-50° C. In another aspect, the fluorescence intensity of the quenched Au-BSA nanoclusters is measured using a sensor. In a further aspect, the sensor comprises a 375 nm LED attached to a fluorescence flow cell.

In another aspect, the Au-BSA nanoclusters comprise a maximum excitation wavelength of approximately 375 nm and a maximum emission wavelength of approximately 675 nm. In another aspect, the method further includes the step of preparing the Au-BSA nanoclusters prior to mixing the Au-BSA nanoclusters with the water sample. To begin the step of preparing the Au-BSA nanoclusters, the Au-BSA nanoclusters are synthesized by entrapment of Au ions by BSA in a solution and subsequent reduction of the Au ions by adjustment of the pH of the solution to approximately 12. The Au-BSA nanoclusters are then purified via size exclusion chromatography (SEC) using a desalting column. The Au-BSA nanoclusters are then conserved by mixing the Au-BSA nanoclusters with a sodium azide solution.

In a second aspect, a method for determining a concentration of glutaraldehyde in a water-glutaraldehyde mixture using gold-bovine serum albumin (Au-BSA) nanoclusters is provided. In the method, a sample of the water-glutaraldehyde mixture is collected. The sample of the water-glutaraldehyde mixture is mixed with Au-BSA nanoclusters, such that the glutaraldehyde present in the mixture reacts with the Au-BSA nanoclusters and causes fluorescence quenching of the Au-BSA nanoclusters. The sample of the water-glutaraldehyde mixture with the Au-BSA nanoclusters is then incubated for at least 2 minutes, such that the incubation facilitates the reaction of glutaraldehyde with the Au-BSA nanoclusters. A fluorescence intensity of the Au-BSA nanoclusters in the mixture is measured at an emission wavelength of 675 nm. A concentration of glutaraldehyde in the water-glutaraldehyde sample is then determined based on a comparison between the measured fluorescence intensity of the Au-BSA nanoclusters at the emission wavelength of 675 nm with fluorescence intensity values of calibration samples comprising Au-BSA nanoclusters and known glutaraldehyde concentrations.

In another aspect, the determined concentration of glutaraldehyde is accurate for water-glutaraldehyde mixtures having a glutaraldehyde content of 10-1000 ppm. In another aspect, the water in the water-glutaraldehyde mixture is fresh water or salt water. In a further aspect, the salt water in the water-glutaraldehyde mixture is Arabian Gulf Seawater.

In another aspect, the sample of the water-glutaraldehyde mixture and the Au-BSA nanoclusters are incubated in a temperature range of approximately 20-50° C. In another aspect, the fluorescence intensity of the Au-BSA nanoclusters is measured using a sensor. In a further aspect, the sensor comprises a 375 nm LED attached to a fluorescence flow cell.

In another aspect, the Au-BSA nanoclusters comprises a maximum excitation wavelength of approximately 375 nm and a maximum emission wavelength of approximately 675 nm. In another aspect, the Au-BSA nanoclusters are purified using a desalting column prior to mixing the Au-BSA nanoclusters with the sample of the water-glutaraldehyde mixture. In another embodiment, the water-glutaraldehyde mixture comprises a glutaraldehyde-based biocide.

BRIEF DESCRIPTION OF THE DRAWING FIGURES

FIGS. 2A-2B displays calibration curves (FIG. 2A—linear scale.

DETAILED DESCRIPTION OF CERTAIN EMBODIMENTS

By way of overview and introduction, the present application discloses methods for detecting and quantifying glutaraldehyde in water sample. In one or more embodiments, gold-bovine serum albumin (Au-BSA) nanoclusters are synthesized and then purified. The Au-BSA nanoclusters are then mixed with a water sample to form a mixture, and the mixture is incubated. After incubation, a fluorescence intensity of the Au-BSA nanoclusters is measured in the mixture at an emission wavelength 675 nm. The presence of glutaraldehyde in the water sample is then determined by comparing the measured fluorescence intensity of the quenched Au-BSA nanoclusters at the emission wavelength of 675 nm with fluorescence intensity values of calibration samples comprising Au-BSA nanoclusters and known glutaraldehyde concentrations. The method is based on fluorescence quenching of the Au-BSA nanoclusters after exposure to GLUT or GLUT-containing biocide products. By measuring the fluorescence intensity change of Au-BSA nanoclusters at 675 nm in the water sample after exposure to GLUT, the GLUT concentration in the water sample can be determined.

In one or more embodiments, the method can be performed using an online sensor. The online sensor can be used in numerous applications, including for online field measurement of GLUT in a large water pipeline network, for example. In one or more embodiments, the present method can be utilized for determining the presence and concentration of GLUT (e.g., from GLUT-containing biocide products) in fresh water and salt water (e.g., Arabian Gulf Seawater [AGS], and other high salinity salt water).

These and other aspects of the present methods are described in further detail below with reference to the accompany drawing figures, in which one or more illustrated embodiments and/or arrangements of the biocides are shown. The methods of the present application are not limited in any way to the illustrated embodiments and/or arrangements. It should be understood that the methods as shown in the accompanying figures are merely exemplary of the methods of the present application, which can be embodied in various forms as appreciated by one skilled in the art. Therefore, it is to be understood that any structural and functional details disclosed herein are not to be interpreted as limiting the present methods, but rather are provided as a representative embodiment and/or arrangement for teaching one skilled in the art one or more ways to implement the present methods. Further, it should be understood that, as used in the present application, the term "approximately" when used in conjunction with a number refers to any number within 5% of the referenced number, including the referenced number.

Figure 1:
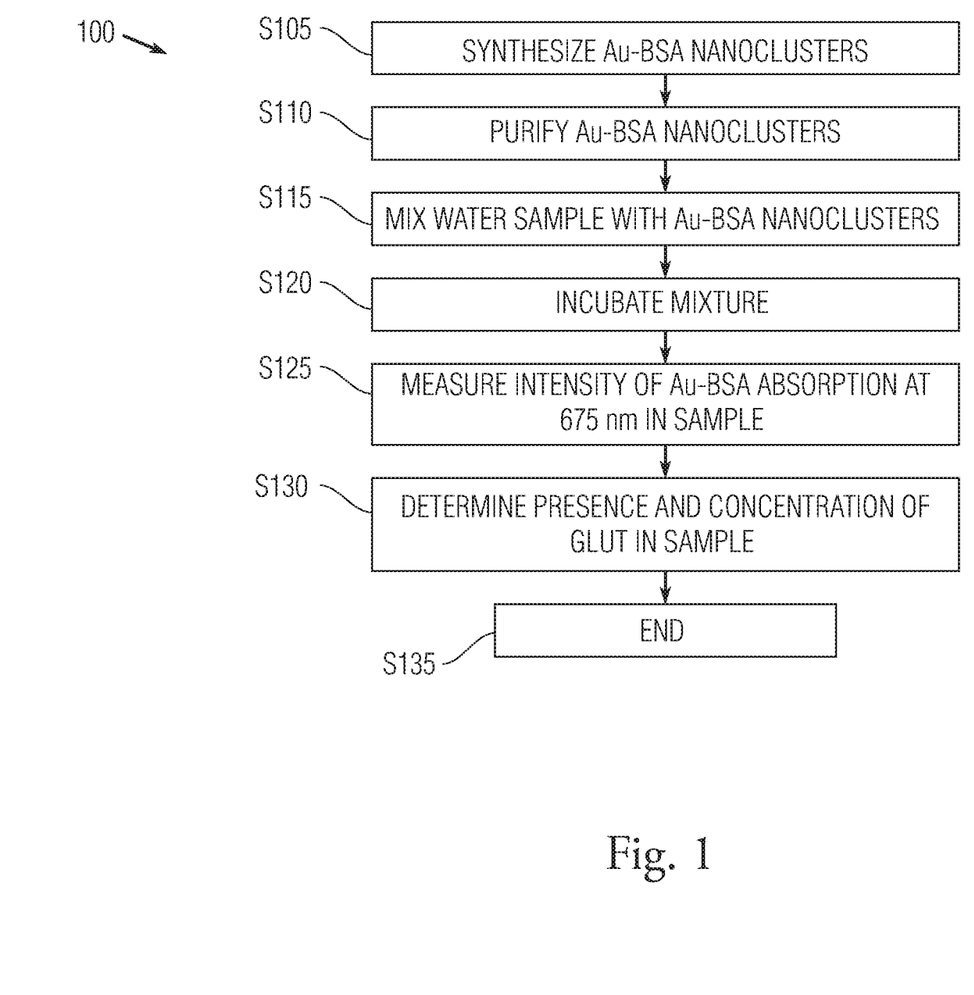
FIG. 1 displays a flow diagram of steps for a method for detecting glutaraldehyde in water sample in accordance with one or more embodiments.

Referring now to FIG. 1, a flow diagram of steps for a method 100 for detecting glutaraldehyde in water sample is provided in accordance with one or more embodiments. The method 100 begins at step S105 where gold-bovine serum albumin (Au-BSA) nanoclusters are synthesized.

The synthesis of the gold-BSA nanoclusters is based upon the ability of BSA to sequester gold ions in solution and thereby entrap them. After the entrapment, the ability of BSA molecules to reduce the gold ions is activated by adjusting the pH of the reaction mixture to approximately 12. The progressive reduction of the entrapped gold ions produces the Au-BSA nanoclusters. These nanoclusters of metallic gold (Au) are stabilized by the BSA molecules that form a protein shell around the gold clusters. In one or more embodiments, the gold nanoclusters consisted of 25 gold atoms and thus are very small and have unique fluorescent properties.

In one or more embodiments, to make the Au-BSA nanoclusters, solid gold chloride is dissolved in demineralized water in a first container to make a gold chloride solution. BSA is then dissolved in demineralized water in a second container to make a BSA solution. Sodium azide is then dissolved in demineralized water in a third container to make a sodium azide solution. The gold chloride solution and BSA solution are then equilibrated at approximately 37° C. in a preheated incubator or oven. The gold chloride solution is then added to the BSA solution under vigorous stirring of the BSA solution to form a reaction mixture, while keeping both the mixture at 37° C. A sodium hydroxide solution is then added to the reaction mixture and the reaction mixture is incubated at 37° C. for at least 12 hours, while stirring is continued, resulting in a solution comprising Au-BSA nanoclusters.

At step S110, the Au-BSA nanoparticles are purified. Specifically, in one or more embodiments the resulting solution comprising the Au-BSA nanoclusters is cleaned up by size exclusion chromatography (SEC) using a desalting column. For instance, an ECONO-PAC® 10DG desalting column or other desalting column known in the art can be used. In one or more embodiments, the Au-BSA nanoparticles can be purified by performing the desalting protocol provided in ECONO-PAC® 10DG Columns Instruction Manual Catalog Number 732-2010 by Biorad, which is hereby incorporated by reference. In at least one alternative embodiment, the Au-BSA nanoparticles can be purified using other methods known in the art, such as via dialysis methods using distilled water.

In one or more embodiments, once the Au-BSA nanoparticles are purified, the Au-BSA nanoparticles can be optionally stored (conserved) by adding a sodium azide solution to the Au-BSA nanoparticles solution. In one or more embodiments, the resulting mixture can be stored at approximately 4° C. (long term storage). In one or more embodiments, the Au-BSA nanoparticles are diluted 5-10 times to reduce the concentration of the synthesized Au-BSA nanoparticles in the solution to approximately 3-6 µM.

With continued reference to FIG. 1, at step S115, the Au-BSA nanoparticles (e.g., purified Au-BSA nanoparticles) are mixed with a water sample to form a mixture. The water sample comprises or is suspected of comprising glutaraldehyde (GLUT) or a GLUT-containing biocide. The water sample can be a freshwater sample or a saltwater sample, such as Arabian Gulf Seawater (AGS). In one or more embodiments, the water sample can be collected from an existing body of water, or from a water treatment facility or water distribution network known to comprise GLUT or GLUT-based biocides. In one or more embodiments, a predetermined volume of the water sample and the Au-BSA nanoclusters solution are mixed together. For example, in one or more embodiments, approximately 100 µl of the Au-BSA nanoclusters solution is mixed with approximately 1000 µl water sample that comprises glutaraldehyde (GLUT) or a GLUT-containing biocide. The biocide can be any GLUT-containing biocide known in the art, such as DURACIDE 9229 (20-60% GLUT) or BOITREAT 4000 (25-50% GLUT). In one or more embodiments, the water sample has a glutaraldehyde content of approximately 10-1000 ppm. In one or more embodiments, the concentrations of Au-BSA nanoclusters in the mixture is approximately 3-6 µM.

At step S120 the mixture of Au-BSA nanoparticles and the water sample is incubated. In one or more embodiments, the mixture should be incubated for at least 2 minutes to ensure adequate time for the reaction between GLUT and the Au-BSA nanoparticles. In the reaction, GLUT interrupts the interaction of BSA and Au atoms in the nanoclusters due to the chemical crosslinking properties of GLUT. As such, when GLUT is present in the mixture, the reaction of GLUT with the Au-BSA nanoclusters renders the Au atoms isolated from the BSA protection, and thus the fluorescence of the Au-BSA nanoclusters is quenched. In one or embodiments, the mixture is incubated in a temperature range of approximately 20-50° C. In one or more preferred embodiments, the mixture is incubated for approximately 2-10 minutes in a temperature range of approximately 35-50° C. In one or more embodiments, the mixture is incubated for approximately 2 minutes at a temperature of approximately 50° C. In at least one embodiment, the mixture is incubated at approximately 37° C. In at least one embodiment, the mixture is incubated at approximately room temperature (approximately 20° C.).

With continued reference to FIG. 1, at step S125, a fluorescence intensity of the Au-BSA nanoclusters in the mixture is measured at an emission wavelength of 675 nm. The Au-BSA nanoclusters comprise a maximum excitation wavelength of approximately 375 nm and a maximum emission wavelength of approximately 675 nm. As mentioned above, the reaction of GLUT with the Au-BSA nanoclusters quenches the fluorescence of the Au-BSA nanoclusters. As such, in embodiments in which GLUT is present in the mixture, the resulting measured fluorescence signal intensity of the Au-BSA nanoclusters is correlated with GLUT concentration. In the present methods, the GLUT concentration in the water sample can be accurately determined for water samples comprising GLUT in a range of approximately 10-1000 ppm. In other words, the present methods have a dynamic range of approximately 10-1000 ppm for GLUT. This concentration range covers the normal biocide treatment concentration and residual concentration encountered in water treatment facilities and distribution networks in oil and gas industry.

Figure 2A:
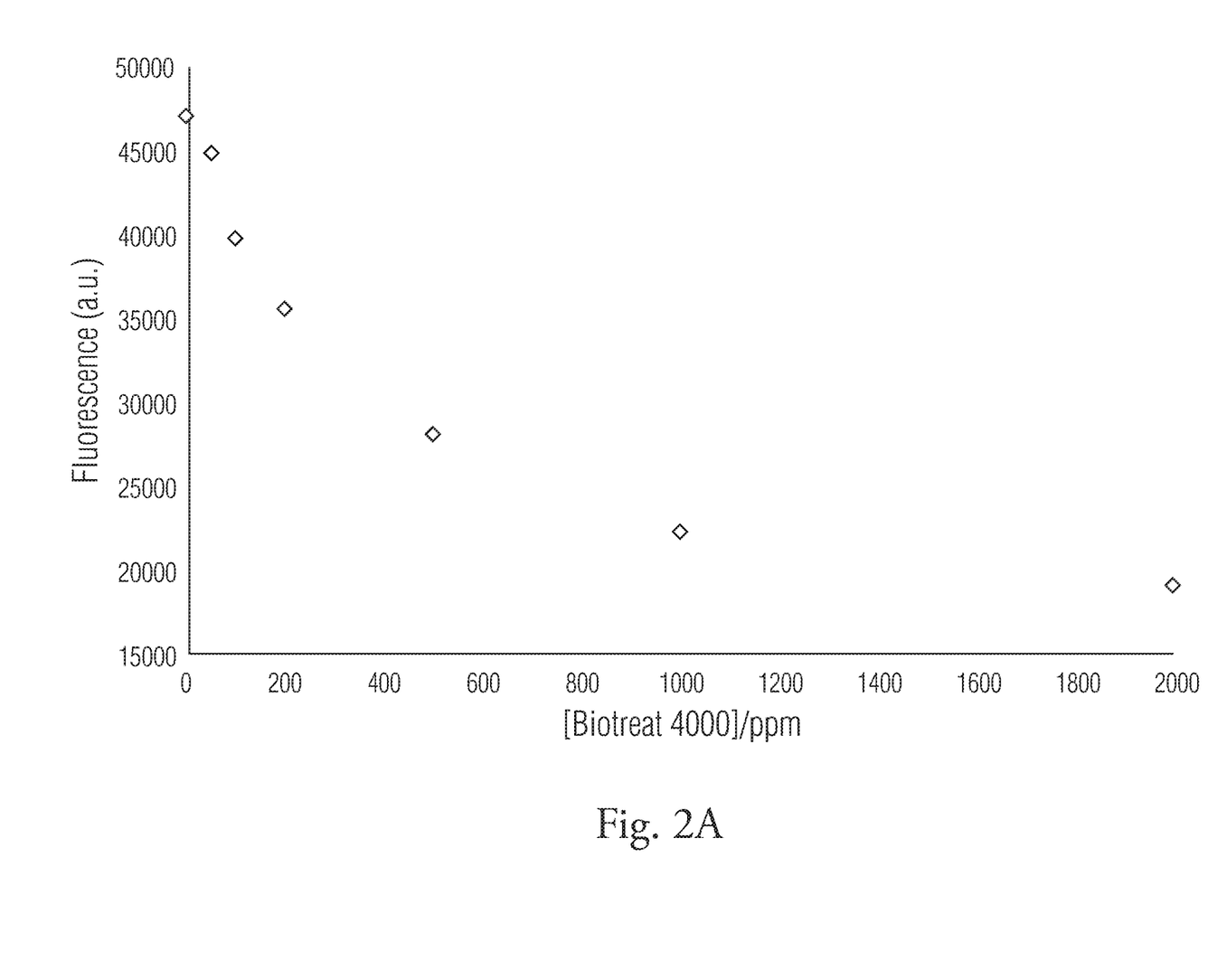
Figure 2B:
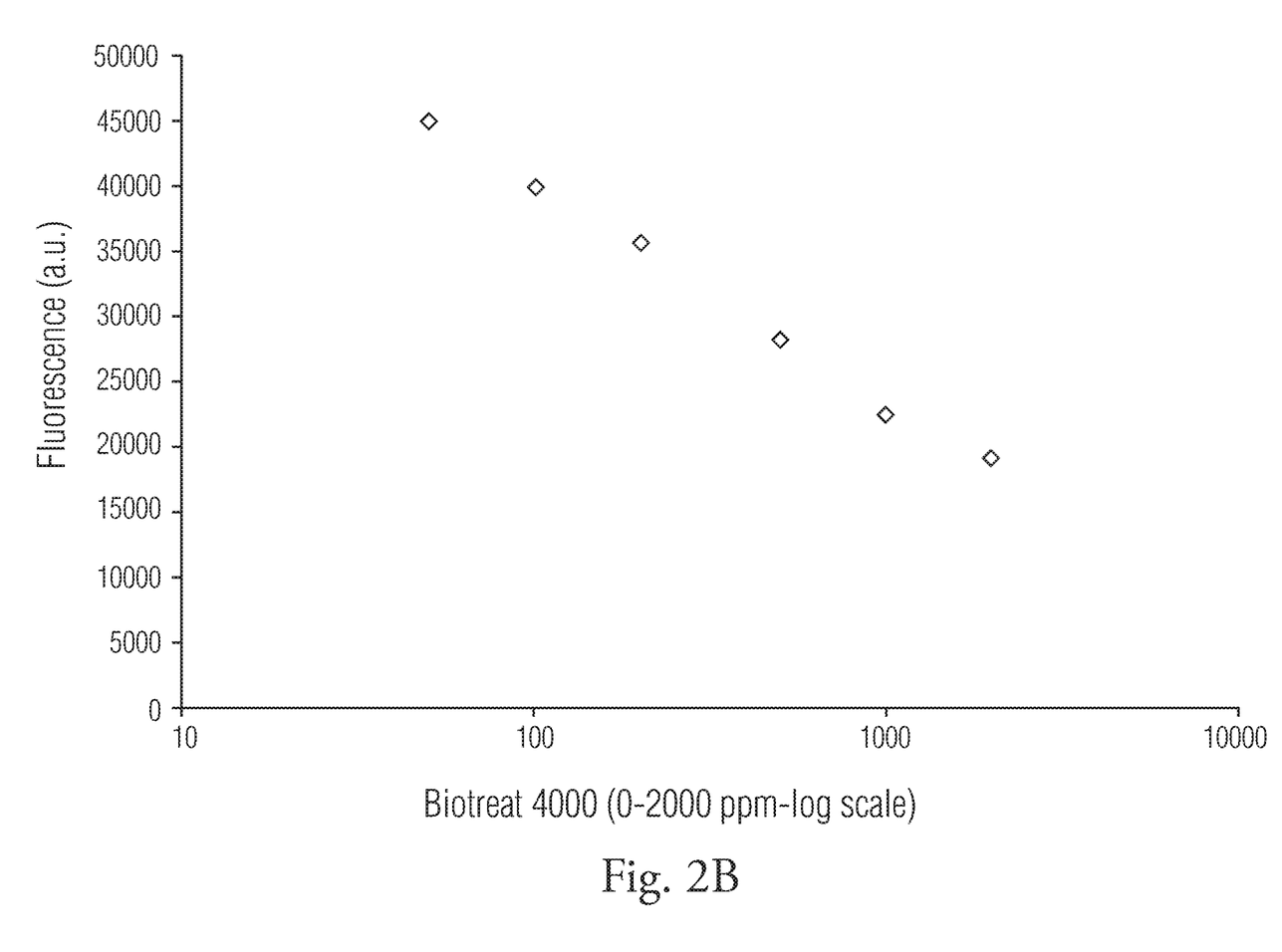
FIG. 2B—log scale) for 0-2000 ppm of BIOTREAT 4000 (GLUT-based biocide), showing the fluorescence intensity of the Au-BSA nanoparticles following mixing and incubation for 10 minutes at 37° C. with various concentrations of BIOTREAT 4000 (GLUT-based biocide) in accordance with one or more embodiments.

At S130 the concentration of GLUT in the water sample is determined. To begin step S130, correlation equation (or calibration curve) is established between the known GLUT concentrations and fluorescence intensity of the quenched Au-BSA nanoclusters. As determined by the inventors, fluorescence quenching of the Au-BSA nanoclusters is correlated with the concentration of GLUT in the water sample. As such, based on this correlation, a calibration curve is established between the known GLUT concentration in given samples and fluorescence intensity of the quenched Au-BSA nanoclusters. For example, FIGS. 2A-2B shown example calibration curves for the GLUT concentration in a GLUT-based biocide, BIOTREAT 4000, and the fluorescence intensity of the Au-BSA nanoclusters. As shown in the graph of FIG. 2B, a linear relationship between the concentrations of GLUT-based biocide product (log 10) and fluorescence intensity of Au-BSA is established. Using the established calibration curve, the concentration of GLUT in the water sample is determined by matching the measured fluorescence intensity of the quenched Au-BSA nanoclusters at the emission wavelength of 675 nm with its fluorescence intensity value on the curve and the corresponding GLUT concentration value on the curve. For instance, in the example shown in graph of FIG. 2B, when the fluorescence intensity measurement of the Au-BSA nanoclusters at the emission wavelength of 675 nm is approximately 40,000 a.u. (arbitrary units), the determined concentration of the GLUT-based biocide BIOTREAT 4000 in the water sample was approximately 100 ppm.

In one or more embodiments, the detection range for GLUT concentration in the sample is between approximately 10 and 1000 ppm. After the concentration of GLUT in the water sample is determined, the method ends at step S135.

Figure 3A:
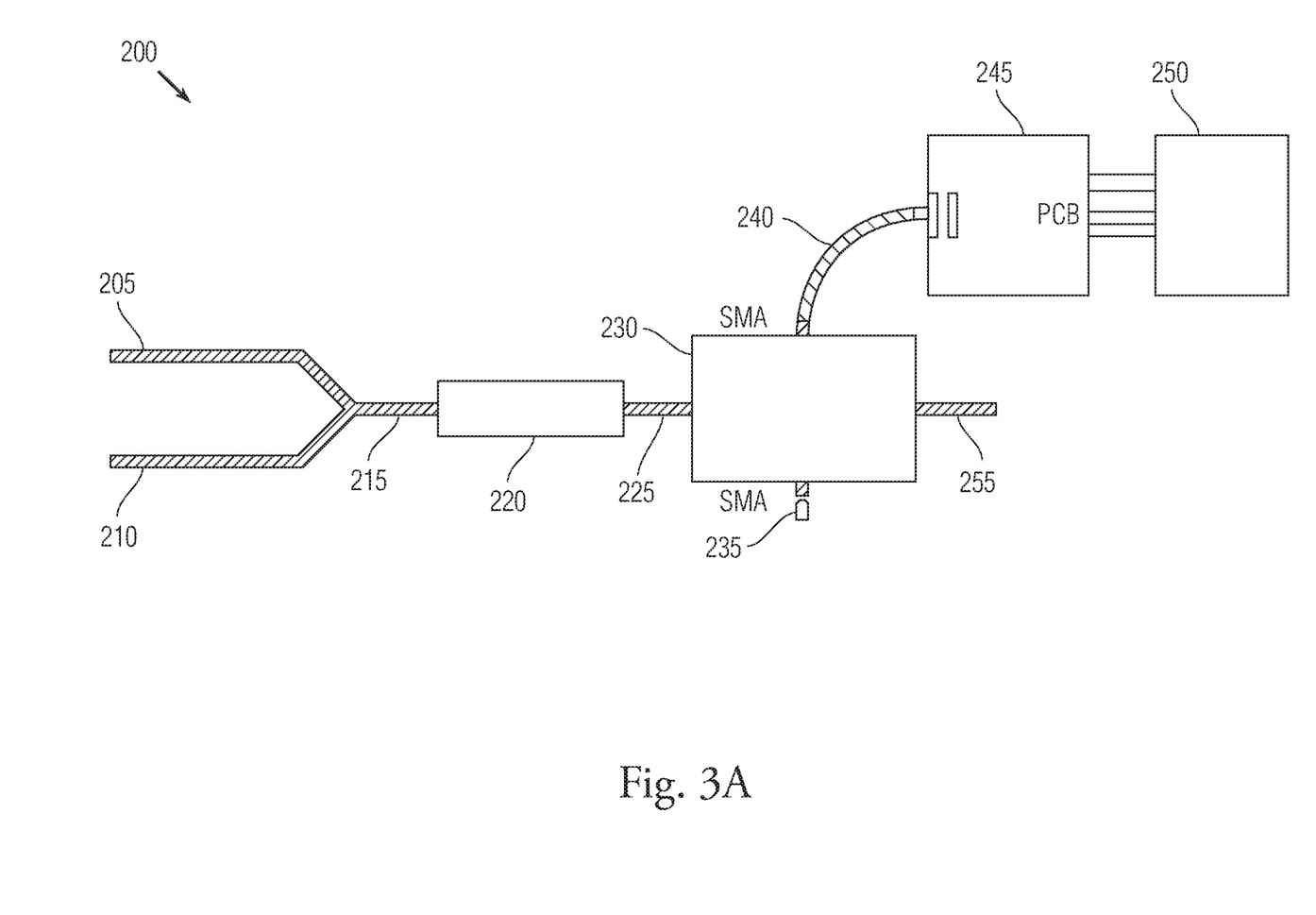
FIGS. 3A-3B display diagrams of aspects of an exemplary GLUT sensor in accordance with one or more embodiments.
Figure 3B:
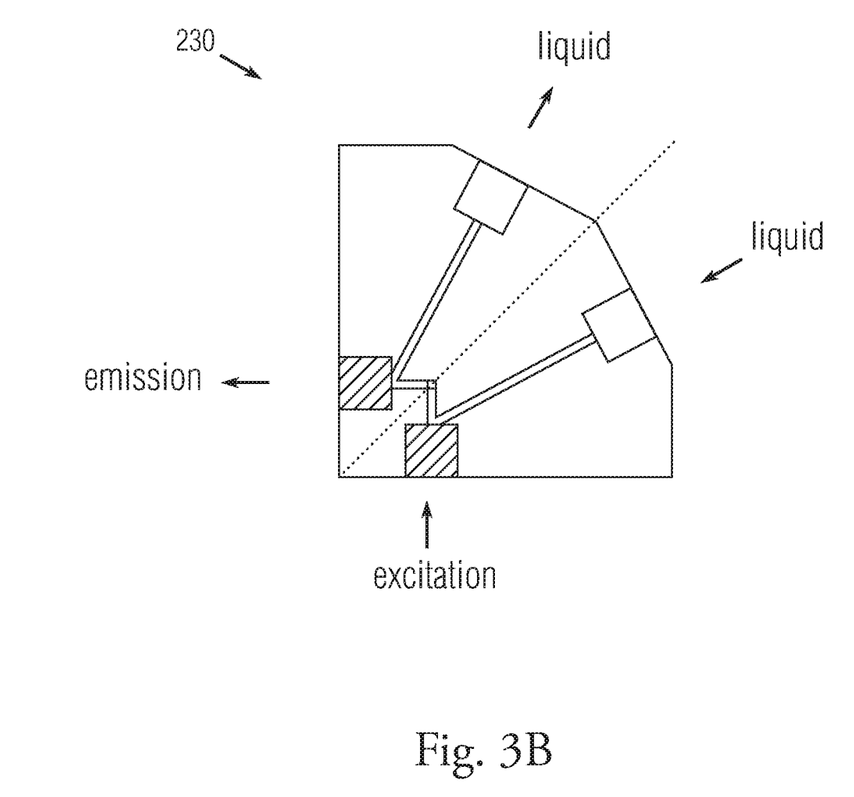

In at least one embodiment, steps S115-S135 can be completed using a sensor. In FIGS. 3A-3B, various aspects of an exemplary GLUT sensor 200 for the present methods are shown. With reference to FIG. 3A, the sensor 200 comprises a sample reservoir 205 for the water sample comprising GLUT and a reservoir 210 for the Au-BSA nanoclusters. The sensor 200 also includes a first conduit 215 for transferring the water sample comprising GLUT and Au-BSA nanoclusters from their respective reservoirs to a mixing coil 220. In the mixing coil 220, the water sample comprising GLUT and the Au-BSA nanoclusters are mixed and incubated (steps S115 and S120). Following incubation, the mixture is transferred via a second conduit 225 to fluorescence flow cell 230. FIG. 3B shows a diagram of various aspects of a fluorescence flow cell 230 in accordance with one or more embodiments.

Referring back to FIG. 3A, the sensor 200 further includes a 375 nm light-emitting diode (LED) 235 that is attached to the fluorescence flow cell 230. In the fluorescence flow cell 230, the mixture comprising the Au-BSA nanoclusters is exposed to the light emitted by the LED 235 to produce fluorescence. In at least one embodiment, a laser can be used for the excitation of the Au-BSA nanoclusters to improve precision for the fluorescence measurement. In one or more embodiments, the flow cell 230 has an excitation path length of approximately 6 mm. When the fluorescence of the Au-BSA nanoclusters is collected by the flow cell 230, it is transported via a patch cable 240 (e.g., 1.5 mm patch cable with an SMA connector) to a microcontroller 245 (e.g., printed circuit board [PCB] microcontroller). A micro-processor platform 250 (e.g., Feather, Arduino technology) can process the analogue signals and provide pulses in order to measure the fluorescence signal intensity of the Au-BSA nanoclusters (step S125). After the fluorescence of the Au-BSA nanoclusters has been measured and the concentration of GLUT in the sample has been determined, the mixture of the water sample and the Au-BSA nanoclusters is passed out of the flow cell 230 via a third conduit 255 and can be disposed of as waste. The GLUT sensor 200 can be applied in any water treatment or distribution systems, providing online monitoring of GLUT-based biocide residual concentration and ensuring adequate biocide treatment for microbial control.

In one or more embodiments, the sensor 200 is an online sensor that is operatively connected to a water treatment facility or water distribution network, for example, such that real-time measurements of GLUT in the water treatment facility or water distribution network can be determined. In one or more embodiments, the sensor can also be configured to transmit measurements (wired or wireless transmissions) and data to a control center remote from the sensor 200.

In at least one embodiment, steps S125-S130 can be performed with instruments other than a sensor. For example, lab-based instruments with a fluorescence detector can be used to measure the fluorescence intensity of the Au-BSA nanoclusters. Such lab-based instruments can include, for example, fluorometers, spectrofluorometers, fluorescence spectrometers, spectrophotometers, and spectrometers with fluorescence detectors. An example of suitable fluorescence spectrophotometers are PERKIN ELMER FL 6500 and FL 8500.

Figure 4:
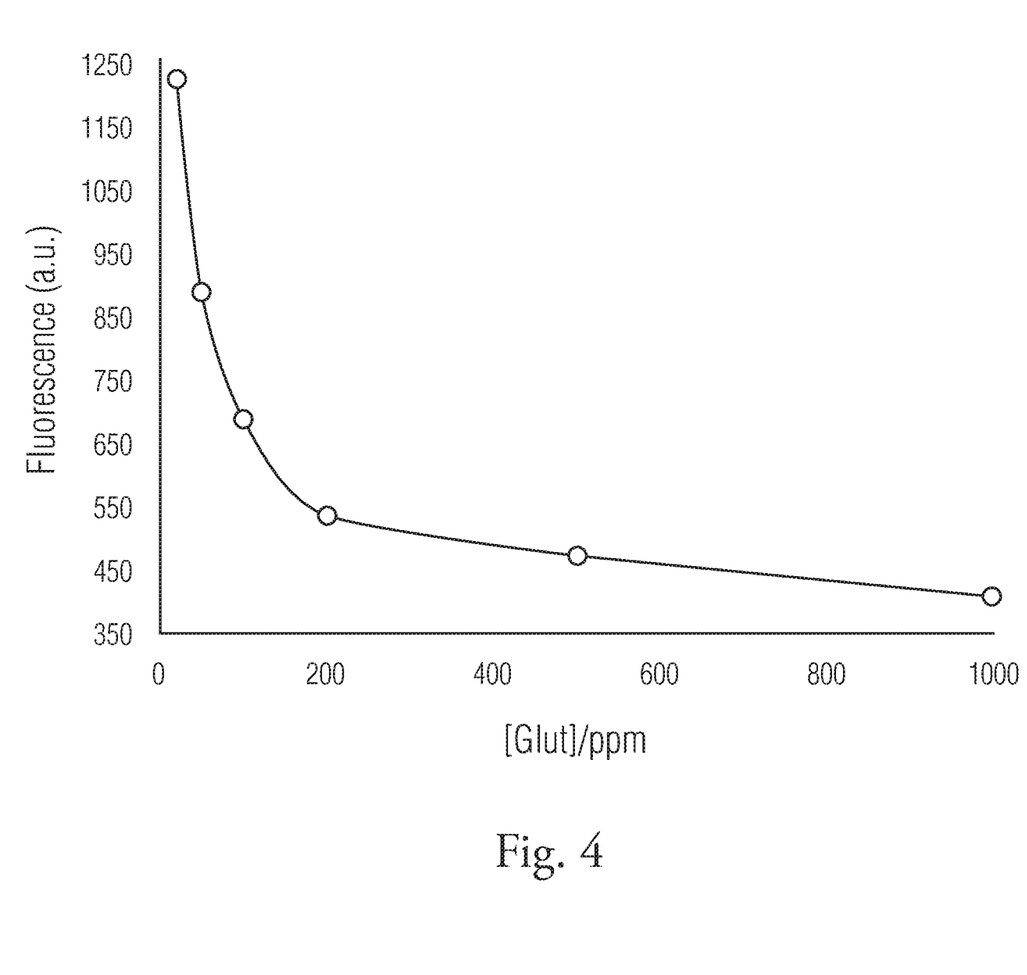
FIG. 4 displays a graph showing the correlation of fluorescence measurement data of Au-BSA nanoclusters quenched with GLUT and GLUT concentration, where the measurements were performed with sensor in accordance with one or more embodiments.

FIG. 4 shows exemplary fluorescence measurement data of Au-BSA nanoclusters quenched with GLUT, where the measurements were performed with sensor 200 in accordance with one or more embodiments. In FIG. 4, the fluorescence of Au-BSA nanoparticles solutions at 10-1000 ppm of GLUT is shown. As shown from the graph the fluorescence of the Au-BSA samples is easily measured using the sensor in the relevant range of GLUT concentrations in the saltwater treatment facilities and distribution networks. Specifically, as shown by the graph of FIG. 4, the data validated that the GLUT sensing via fluorescence measurement of Au-BSA nanoclusters with the sensor is effective for monitoring biocide concentrations at the relevant range in the saltwater treatment facilities and distribution networks (10-1000 ppm GLUT).

Various aspects of the present methods can be further understood through the following examples.

Example 1

In this example, fluorescence quenching of Au-BSA nanoclusters in accordance with one or more embodiments of the present application is validated using a biocide product comprising GLUT in demineralized water. A biocide product (Biotreat 4000) containing 25-50% GLUT was used in this experiment. The product was diluted in demineralized water into 0, 50, 100, 200, 500, 1000, 2000 ppm of the biocide. After mixing the biocide (diluted with demineralized water) with a Au-BSA nanoclusters solution, the samples were incubated for a short time (maximum of 10 minutes) at 37° C. to support the reaction (quenching) between the GLUT in the biocide formulation and the Au-BSA nanoclusters. FIGS. 2A-2B show the resulting calibration curves based on the fluorescence intensity of Au-BSA nanoclusters, with the BIOTREAT 4000 concentrations on a linear scale (FIG. 2A) and on a logarithmic scale (FIG. 2B). As shown by the calibration curves, the fluorescence intensity of quenched Au-BSA nanoclusters showed a linear relationship with the concentrations of biocide product, up to 2000 ppm, or 1000 ppm of GLUT (assuming 50% GLUT in the biocide).

Example 2

This example provides validation of fluorescence quenching of Au-BSA nanoclusters in Arabian Gulf Seawater (AGS) in accordance with one or more embodiments of the present application. AGS is widely used in the Middle East region for reservoir injection for pressure maintenance of oil reservoirs. The treated AGS is transported through complex pipeline network for reservoir injection, and the microbial activities in the AGS are controlled by biocide treatment. The fluorescence quenching assay of Au-BSA nanoclusters was validated in AGS, which has salinity around 57,000 mg/L. AGS has much higher salinity than average salt water in the world's oceans (approximately 35,000 mg/L).

Figure 5:
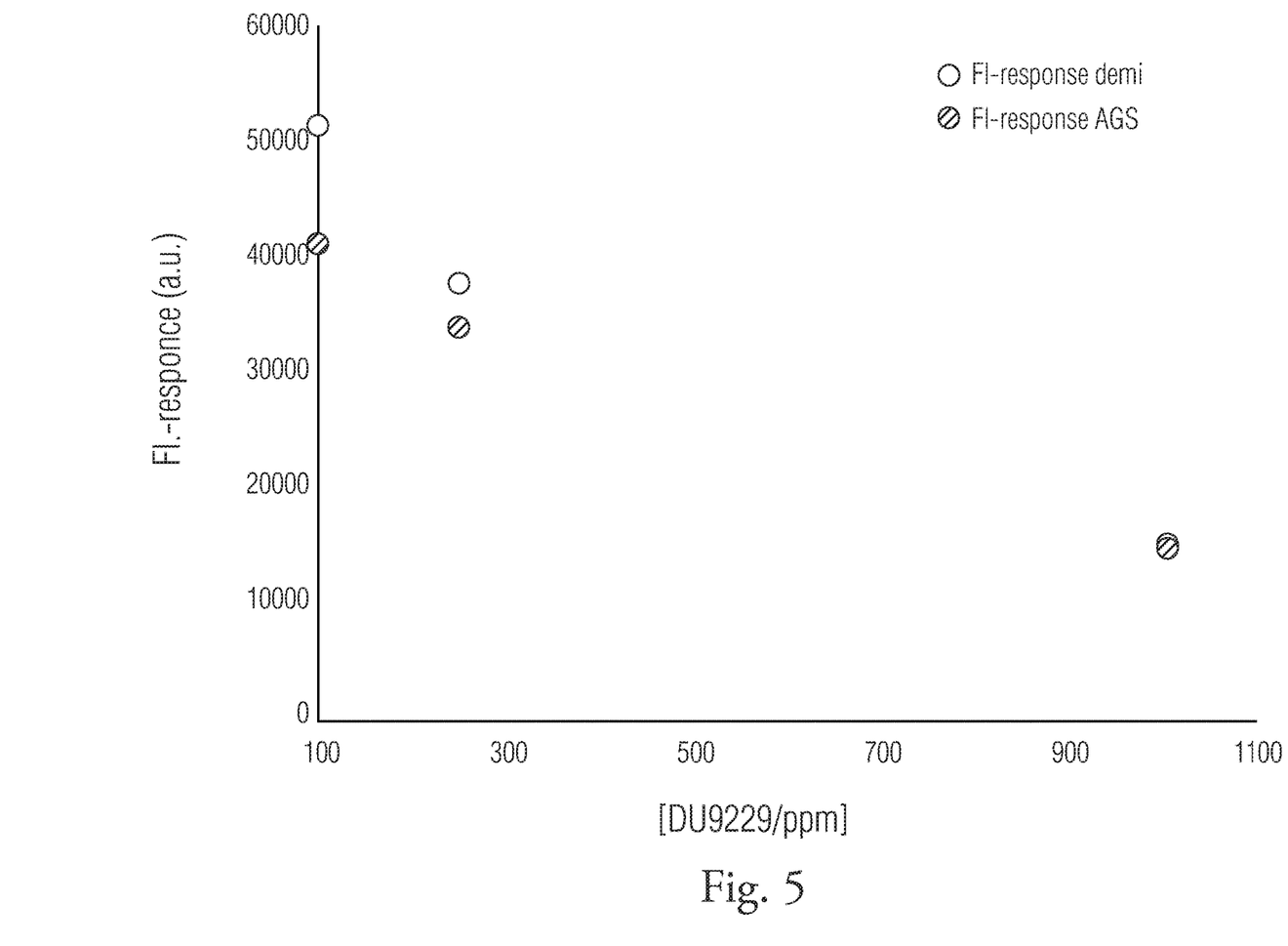
FIG. 5 displays a graph showing the fluorescence response of the Au-BSA nanoparticles at various concentrations of DURACIDE 9229 (GLUT-based biocide) prepared in demineralized water (demi water) and Arabian Gulf Seawater (AGS) in accordance with one or more embodiments.

The influence of AGS was tested for the inhibition of the fluorescence of Au-BSA nanoclusters at various concentrations of a GLUT-based biocide, DURACIDE 9229. DURACIDE 9229 contains 20-60% of GLUT, and samples of 100, 250 and 1000 ppm of DURACIDE 9229 were prepared in demineralized water (demi water) and AGS. The purified Au-BSA nanoclusters solution was diluted 10 times in demi water and AGS. 100 μl of diluted Au-BSA nanoclusters solution was mixed with 1000 μl of each sample containing 100-1000 ppm of DURACIDE 9229. After mixing with the Au-BSA nanoclusters solution, the samples were incubated for 10 minutes at 37° C. to support the reaction between the GLUT in the biocide formulation and the Au-BSA nanoparticles. The fluorescence measurements (at emission wavelength of 675 nm) of the Au-BSA-GLUT samples in the two different media (demi water and AGS) are presented in FIG. 5. As shown in the graph of FIG. 5, AGS caused a decrease in fluorescence signal as compared to demi water. However, a clear relation between the concentration of DURACIDE 9229 and the fluorescence signal of Au-BSA nanoparticles was still observed. The dynamic range of the signal inhibition observed in AGS was sufficient for a successful assay.

Example 3

In this example, an exemplary procedure for synthesizing and purifying Au-BSA nanoclusters is provided in accordance with one or more embodiments.

First, 17 mg of gold chloride is dissolved in 5 ml of demineralized water and gently agitated until the solid material is completely dissolved. The resulting gold chloride solution (10 mM, 3.4 mg/ml; volume 5.0 ml) is protected from light if it is not used immediately.

Second, 250 mg of BSA is dissolved in 5 ml of demineralized water and gently agitated until the solid material is completely dissolved. The resulting BSA solution (50 mg/ml; volume 5.0 ml) is stored at 4° C. if not used immediately.

Third, 0.5 g of sodium azide is dissolved in 5 ml of demineralized water and gently agitated until the solid material is completely dissolved. The resulting sodium azide solution (10 wt %, 5 ml) is stored at 4° C.

To prepare the Au-BSA nanoparticles, the gold chloride solution (5 ml) and the BSA solution (5 ml) are equilibrated at 37° C. in a preheated incubator or oven. The gold chloride solution is then gently added to the BSA solution under vigorous stirring of the BSA solution to form a mixture, while keeping both solutions at 37° C. After 2 minutes, 0.5 ml of a sodium hydroxide solution is added to the mixture and the reaction mixture is subsequently incubated at 37° C. for at least 12 hours, while stirring is continued.

The resulting Au-BSA nanoparticles (deep brown solution) is then purified via size exclusion chromatography (SEC) using an ECONO-PAC® 10DG desalting column. To perform this, the desalting protocol provided in ECONO-PAC® 10DG Columns Instruction Manual Catalog Number 732-2010 by Biorad is provided. The yield of one run with this desalting column is 4.5 ml Au-BSA nanoparticles solution.

To conserve and store the purified Au-BSA nanoparticles long-term, 20 µl of the sodium azide solution is added to and mixed with the purified Au-BSA solution from the previous step. The resulting mixture is then stored at 4° C.

In view of the foregoing disclosure, the present application provides methods for detecting and/or quantifying GLUT in a water sample. More specifically, in instances in which it is unknown or merely suspected that the water sample comprises GLUT, the present methods can determine whether GLUT is present in water sample when GLUT is present in the water sample at a concentration of between approximately 10 and 1000 ppm. Additionally, the present methods can accurately determine a concentration of GLUT in the water sample when GLUT is present in the water sample at a concentration of between approximately 10 and 1000 ppm. This is a drastic improvement over conventional measurement tools and systems, which can only detect very low concentrations of GLUT (less than 0.1 ppm) or very high concentrations of GLUT (5000-25000 ppm), both of which are outside of the normal biocide treatment concentration range and residual concentration range in actual water treatment facilities and water distribution network. Additionally, the present method is effective for accurately determining the concentration of GLUT in both freshwater and saltwater samples (e.g., AGS, which has a salinity of approximately 57,000 mg/L), while previous methods have been limited to freshwater applications. The present method is also effective for detecting and quantifying both pure GLUT and GLUT from GLUT-containing biocide products. In contrast, many existing measurement products are only validated for measuring pure GLUT.

Although much of the foregoing description has been directed to methods for detecting glutaraldehyde in water sample, the methods disclosed herein can be similarly deployed and/or implemented in scenarios, situations, and settings far beyond the referenced scenarios. It should be further understood that any such implementation and/or deployment is within the scope of the methods described herein.

It is to be further understood that like numerals in the drawings represent like elements through the several figures, and that not all components and/or steps described and illustrated with reference to the figures are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Notably, the figures and examples above are not meant to limit the scope of the present disclosure to a single implementation, as other implementations are possible by way of interchange of some or all the described or illustrated elements. Moreover, where certain elements of the present disclosure can be partially or fully implemented using known components, only those portions of such known components that are necessary for an understanding of the present disclosure are described, and detailed descriptions of other portions of such known components are omitted so as not to obscure the disclosure. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration.

The foregoing description of the specific implementations will so fully reveal the general nature of the disclosure that others can, by applying knowledge within the skill of the relevant art(s), readily modify and/or adapt for various applications such specific implementations, without undue experimentation, without departing from the general concept of the present disclosure. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the disclosure.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

What is claimed is:

1. A method for detecting glutaraldehyde in a water sample in which gold-bovine serum albumin (Au-BSA) nanoclusters have been introduced, comprising:
mixing the water sample with the Au-BSA nanoclusters to form a mixture;
incubating the mixture for 2 to 10 minutes, wherein the glutaraldehyde present in the water sample quenches the Au-BSA nanoclusters;
measuring a fluorescence intensity of the quenched Au-BSA nanoclusters in the mixture at an emission wavelength of 675 nm, wherein the fluorescence intensity of the quenched Au-BSA nanoclusters is measured using a sensor comprising a 375 nm light-emitting diode (LED) attached to a fluorescence flow cell; and
determining a presence of the glutaraldehyde in the water sample by comparing the measured fluorescence intensity of the quenched Au-BSA nanoclusters at the emission wavelength of 675 nm with fluorescence intensity values of calibration samples comprising Au-BSA nanoclusters and known glutaraldehyde concentrations.

2. The method of claim 1, wherein the step of determining the presence of glutaraldehyde in the water sample comprises:
calculating a concentration of glutaraldehyde in the water sample based on the correlation between the known glutaraldehyde concentrations and the fluorescence intensity of the quenched Au-BSA nanoclusters measured at the emission wavelength of 675 nm.

3. The method of claim 2, wherein the water sample has a glutaraldehyde content of 10-1000 ppm.

4. The method of claim 1, wherein the water is fresh water or salt water.

5. The method of claim 4, wherein the salt water is Arabian Gulf Seawater.

6. The method of claim 1, wherein the mixture is incubated in a temperature range of approximately 20-50° C.

7. The method of claim 1, wherein the Au-BSA nanoclusters comprise a maximum excitation wavelength of approximately 375 nm and a maximum emission wavelength of approximately 675 nm.

8. The method of claim 1, further comprising the step of preparing the Au-BSA nanoclusters prior to mixing with the water sample, wherein the step of preparing the Au-BSA nanoclusters comprises:
synthesizing the Au-BSA nanoclusters by entrapment of Au ions by BSA in a solution and subsequent reduction of the Au ions by adjustment of the pH of the solution to approximately 12;
purifying the Au-BSA nanoclusters via size exclusion chromatography (SEC) using a desalting column; and
conserving the Au-BSA nanoclusters by mixing the Au-BSA nanoclusters with a sodium azide solution.

9. A method for determining a concentration of glutaraldehyde in a water-glutaraldehyde mixture using gold-bovine serum albumin (Au-BSA) nanoclusters, the method comprising:
collecting a sample of the water-glutaraldehyde mixture;
mixing the sample of the water-glutaraldehyde mixture with Au-BSA nanoclusters, wherein the glutaraldehyde present in the mixture reacts with the Au-BSA nanoclusters and causes fluorescence quenching of the Au-BSA nanoclusters;
incubating the sample of the water-glutaraldehyde mixture with the Au-BSA nanoclusters for at least 2 minutes, wherein the incubation facilitates the reaction of the glutaraldehyde with the Au-BSA nanoclusters;
measuring a fluorescence intensity of the Au-BSA nanoclusters in the mixture at an emission wavelength of 675 nm, wherein the Au-BSA nanoclusters comprises a maximum excitation wavelength of approximately 375 nm and a maximum emission wavelength of approximately 675 nm; and
determining a concentration of the glutaraldehyde in the water-glutaraldehyde sample based on a comparison between the measured fluorescence intensity of the Au-BSA nanoclusters at the emission wavelength of 675 nm with fluorescence intensity values of calibration samples comprising Au-BSA nanoclusters and known glutaraldehyde concentrations.

10. The method of claim 9, wherein the water-glutaraldehyde mixture has a glutaraldehyde content of 10-1000 ppm.

11. The method of claim 9, wherein the water in the water-glutaraldehyde mixture is fresh water or salt water.

12. The method of claim 11, wherein the salt water in the water-glutaraldehyde mixture is Arabian Gulf Seawater.

13. The method of claim 9, wherein the sample of the water-glutaraldehyde mixture and the Au-BSA nanoclusters are incubated in a temperature range of approximately 35-50° C.

14. The method of claim 9, wherein the fluorescence intensity of the Au-BSA nanoclusters is measured using a sensor.

15. The method of claim 14, wherein the sensor comprises a 375 nm LED attached to a fluorescence flow cell.

16. The method of claim 9, further comprising purifying the Au-BSA nanoclusters using a desalting column prior to mixing the Au-BSA nanoclusters with the sample of the water-glutaraldehyde mixture.

17. The method of claim 9, wherein the glutaraldehyde in the water-glutaraldehyde mixture is from a glutaraldehyde-based biocide.

* * * * *